US009096495B2

(12) United States Patent
Anelli et al.

(10) Patent No.: US 9,096,495 B2
(45) Date of Patent: Aug. 4, 2015

(54) PROCESS FOR THE PREPARATION OF TRIIODINATED CARBOXYLIC AROMATIC DERIVATIVES

(75) Inventors: Pier Lucio Anelli, Colleretto Giacosa (IT); Marino Brocchetta, Pavia (IT); Roberta Fretta, Colleretto Giacosa (IT); Luciano Lattuada, Colleretto Giacosa (IT); Armando Mortillaro, Colleretto Giacosa (IT)

(73) Assignee: Bracco Imaging S.P.A., Milan (IT)

( * ) Notice: Subject to any disclaimer, the term of this patent is extended or adjusted under 35 U.S.C. 154(b) by 294 days.

(21) Appl. No.: 13/143,225

(22) PCT Filed: Mar. 12, 2010

(86) PCT No.: PCT/EP2010/053186
§ 371 (c)(1),
(2), (4) Date: Jul. 5, 2011

(87) PCT Pub. No.: WO2010/105983
PCT Pub. Date: Sep. 23, 2010

(65) Prior Publication Data
US 2011/0275850 A1 Nov. 10, 2011

(30) Foreign Application Priority Data
Mar. 20, 2009 (EP) .................................... 09155695

(51) Int. Cl.
C07C 233/06 (2006.01)
C07C 237/46 (2006.01)
C07C 231/02 (2006.01)
C07C 231/10 (2006.01)

(52) U.S. Cl.
CPC ............ *C07C 237/46* (2013.01); *C07C 231/02* (2013.01); *C07C 231/10* (2013.01)

(58) Field of Classification Search
CPC .......................... A61K 49/0438; C07C 311/08
USPC ............................................... 560/41, 45, 47
See application file for complete search history.

(56) References Cited

U.S. PATENT DOCUMENTS

| 4,001,323 | A | * | 1/1977 | Felder et al. ................ 564/153 |
| 5,362,905 | A | | 11/1994 | Villa et al. |
| 5,698,739 | A | | 12/1997 | Sovak |
| 2010/0113504 | A1 | * | 5/2010 | Hanessian et al. ............ 514/293 |

FOREIGN PATENT DOCUMENTS

| CN | 1478068 A | 2/2004 |
| DE | 1085648 B | 7/1960 |
| RU | 2060246 C1 | 5/1996 |
| SU | 628813 A3 | 10/1978 |
| WO | 94-14478 A1 | 7/1994 |
| WO | 96-37458 A1 | 11/1996 |
| WO | 96/37459 A1 | 11/1996 |
| WO | 96-37460 A1 | 11/1996 |
| WO | 97-47590 A2 | 12/1997 |
| WO | 98-24757 A1 | 6/1998 |
| WO | 98-28259 A1 | 7/1998 |
| WO | 99-58494 A2 | 11/1999 |
| WO | 02/44132 A1 | 6/2002 |

OTHER PUBLICATIONS

Jager, Ulrich et al., "Fluorsubstituierte 1,2-Thiazetan-3-nn-1-oxide durch Reaktion von Bis(trifluormethyl)keten mit N-Sulfinylaminen", Chem. Ber., vol. 119, 1986, pp. 1127-1132, VCH Veriagsgselschaft mbH, D-6940 Weinheim, XP-002541121.

Chidambaram, Ramakrishnan et al., "Reaction of electron-deficient N-sulfinylanilines with chirala alpha-hydroxy acids: a new process for the synthesis of enantiomerically pure alpha-hydroxy amide", Tetrahedron Letters, vol. 41 (32), 2000, pp. 6017-6020, Elsevier Science Ltd., Amsterdam, XP004243504.

Chidambaram, Ramakrishnan et al., "A Practical Synthesis of the RARc Agonist, BMS-270394", Organic Process Research & Development, vol. 6(5), 2002, pp. 632-636, http://pubs.acs.org, XP002541120.

Hanessin Stephen et al., "omega-Alkoxy analogues of SAHA (vorinostat) as inhibitors of HDAC: A study of chain-length and stereochemical dependence", Bioorganic Medicinal Chemistry Letters, vol. 17(22), 2007, pp. 6261-6265, www.sciencedirect.com, Elsevier Ltd., XP022297139, ISSN: 0960-894X.

Shin, Jai Moo et al., "New Facile Synthesis of alpha-Hydroxyamides: intermolecular and Intramolecular Catalysts in the Reaction of alpha-Hydroxycarboxylic Acids with N-Sulfinylamines", Tetrahedron Letters, vol. 27(17), 1986, pp. 1921-1924, Pergamon Press Ltd., Great Britain, XP-002541119, SSN: 0040-4039.

PCT International Search Report for PCT/EP2010/053186, mail date May 21, 2010.

PCT Written Opinion of the International Searching Authority for PCT/EP2010/053186, mail date May 21, 2010.

Office Action for Chinese application No. 201080008147.5, mail date Jul. 3, 2013 (English translation).

Chidambaram, Ramakrishnan et al., Reaction of electron-deficient N-sulfinylanilines with chiral alpha-hydroxy acids: a new process for the synthesis of enantiomerically pure alpha-hydroxy amides, Tetrahedron Letters, vol. 41, 2000, pp. 6017-6020, Elsevier Science Ltd.

Office Action for Canadian application No. 2,755,650, mail date Dec. 6, 2012.

(Continued)

*Primary Examiner* — Sudhakar Katakam
*Assistant Examiner* — Pancham Bakshi
(74) *Attorney, Agent, or Firm* — VIVICAR Law, PLLC

(57) ABSTRACT

The present invention relates to a process for the preparation of given carboxamido compounds, in particular of 2,4,6-triiodoisophthalic acid derivatives, as useful intermediates for the preparation of X-ray contrast media among which is iopamidol. The said process comprises reacting suitable N-sulfinyl intermediate compounds with a commercially available α-hydroxyacid or a salt thereof.

15 Claims, No Drawings

(56) References Cited

OTHER PUBLICATIONS

Decision on Grant Patent for Invention for Russian application No. 2011142308, mail date Dec. 12, 2013 (English translation).

Office Action for Japanese application No. 2012-500197, mail date Jan. 21, 2014 (English translation).

Gijsen, Harrie J.M. et al., "Optimisation of the Preparation and Isolation of 5-Amino-2,4,6-triiodoisophthalic Acid Dichloride", Organic Process Research & Development, 1999, vol. 3, No. 1, pp. 38-43, American Chemical Society and Royal Society of Chemistry.

Greene, Theodora W., "Protective Groups in Organic Synthesis", 1st Edition, Chapter 2: Protection for the Hydroxyl Group Including 1,2- and 1,3- Diols, 1981, John Wiley & Sons, Inc., ISBN 0-471-05764.9.

Hanessian, Stephen et al., "Exploring alternative Zn-binding groups in the design of HDAC inhibitors: Squaric acid, N-hydroxyurea, and oxazoline analogues of SAHA", Bioorganic & Medicinal Chemistry Letters, 2006, vol. 16, pp. 4784-4787, www.sciencedirect.com, Elsevier Ltd.

The MERCK Index, 13th Edition, Editors: Maryadele J. O'Neil et al., Nos. 5071 and 5073, 2001, Merck & Co., Inc., Whitehouse Station, NJ, ISBN No. 0911910-13-1.

Park, Koon Ha et al., "Convenient Synthesis of N-Sulfinylamines Catalytic Effects of Tertiary Amines", Bull. Korean Chem. Soc., 1990, vol. 11, No. 6, pp. 494-496, Department of Chemistry, College of Arts and Sciences, Chung Nam National University, Taejeon, 305-764 Korea.

Pillai, K.M.R. et al., "Heterocyclic Nonionic X-ray Contrast Agents. 3. The Synthesis of 5-[4-(Hydroxymethyl)-2-oxo-3-oxazolidinyl]-2,4,6-triiodo-1,3-benzene-dicarboxamide Derivatives", Journal of Organic Chemistry, 1994, vol. 59, No. 6, pp. 1344-1350, American Chemical Society.

Office Action for Australian application No. 2010224945, mail date Apr. 8, 2014.

Office Action (Second) for Chinese application No. 201080008147.5, mail date Mar. 5, 2014 (English translation).

Office Action (Third) for Chinese application No. 201080008147.5, mail date Aug. 5, 2014 (English translation).

Office Action for Israeli application No. 215,209, mail date Jul. 29, 2014 (English translation).

Office Action for Korean application No. 10-2011-7020473, mail date Dec. 17, 2012 (English translation).

Notice of Grant for Korean application No. 10-2011-7020473, mail date Aug. 19, 2013 (English translation).

* cited by examiner

PROCESS FOR THE PREPARATION OF TRIIODINATED CARBOXYLIC AROMATIC DERIVATIVES

CROSS-REFERENCE TO RELATED APPLICATIONS

This application is the national stage application of corresponding international application number PCT/EP2010/053186 filed Mar. 12, 2010, which claims priority to and the benefit of European application no. 09155695.1, filed Mar. 20, 2009, all of which are hereby incorporated by reference.

FIELD OF THE INVENTION

The present invention generally relates to a process for the preparation of triiodinated aromatic derivatives comprising the condensation of an amino sulfinyl derivative with a α-hydroxyacid, to achieve the corresponding amido derivatives which represent useful intermediates for the synthesis of x-ray contrast agents.

BACKGROUND ART

Contrast agents, also known as contrast media, are often used during medical imaging examinations to highlight specific parts of the body and make them easier to see. Among them are x-ray contrast media and iodinated non ionic contrast media such as, for instance, diatrizoate, iothalamate, ioxithalamate, metrizoate, iohexyl, iomeprol (The Merck Index, XIII Ed., 2001, No. 5071), iopamidol (The Merck Index, XIII Ed., 2001, No. 5073), iopentol, iopromide, ioversol, ioxilan, iodixanol, iosarcol, iogulamide, ioglunide, iogluamide, acetrizoate, iodamide, iocetamide, ioxaglate, iotrolan, iotasul, iodipamide, iocarmate, iodoxamate, iotroxate, iotrolan, and the like. Additional examples of similar iodinated contrast agents are also described, for instance, in WO 94/14478 (Bracco).

Such compounds may be prepared by a multiplicity of synthetic routes, some of those are characterised by the conversion of aromatic amino derivatives in the corresponding carboxamides, by reaction with a suitable α-hydroxyacid derivative. One representative example of such reaction may be found within the processes for the preparation of Iopamidol as disclosed, for instance, in WO 02/44132, WO 96/37459, WO 96/37460, U.S. Pat. No. 5,362,905, WO 97/47590, WO 98/24757, WO 98/28259 and WO 99/58494. For a general reference to the preparation process of Iopamidol see, e.g., the synthetic path as per Scheme I below:

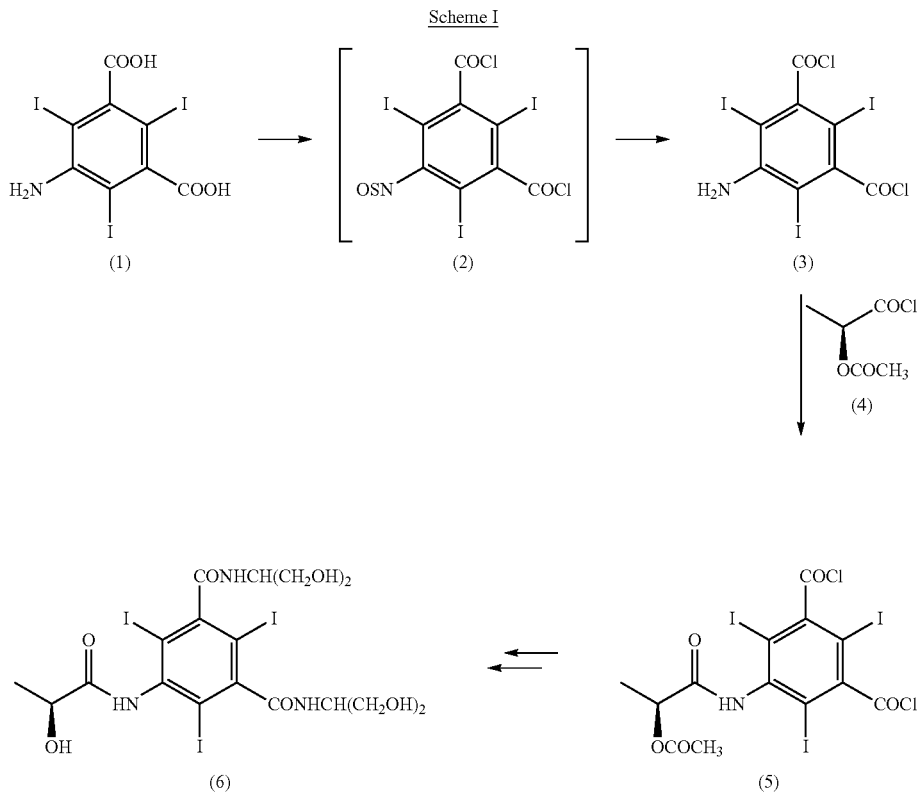

According to Scheme I, the amino derivative of formula (3) is suitably reacted with (2S)-2-(acetyloxy)propanoyl chloride (4), to provide compound (5).

The compound of formula (3) can be obtained, in its turn, by reacting the starting material of formula (1) with a suitable chlorinating agent, e.g. thionyl chloride. Remarkably, and according to what reported in WO 96/37459, an intermediate sulfinyl derivative of formula (2) can be obtained during the chlorination step.

The compound of formula (5) thus obtained is further reacted with the aminoalcohol of choice, in the present case the 2-amino-1,3-propanediol, better known as serinol, and deprotected at the hydroxy group, so to achieve to Iopamidol of formula (6).

Both these latter reactions are carried out according to conventional methods known in the art, either for the preparation of carboxamides by reacting acyl chloride derivatives with amino compounds, or for the cleavage of the acetyl protecting group from the hydroxyl function.

As per the above Scheme I, compound (4) is the activated reactive form of (2S)-2-hydroxy-propanoic acid, commonly known as L-lactic acid, wherein the hydroxy group is suitably protected as therein reported. It has to be noted, in this respect, that the preparation of compound (4) is time consuming as it requires additional synthetic steps starting from commercially available (2S)-2-hydroxy-propanoic acid sodium salt (7), as illustrated in Scheme II below:

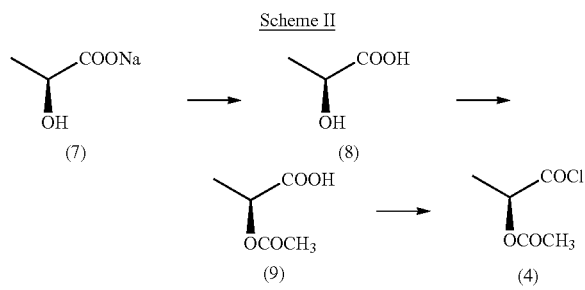

According to Scheme II, the first step is represented by the conversion of compound (7) to L-lactic acid (8), by operating under acidic conditions. The compound thus obtained is then protected at the hydroxy group so as to lead to the corresponding acetylated intermediate (9) that, once recovered and purified, is further converted to the desired acyl chloride (4), by properly functionalizing the carboxylic group with a suitable chlorinating agent, typically thionyl chloride.

Besides the time spending, the protocol according to Scheme II leads to the formation of the desired compound (4) upon a process that contemplates some distillation steps for either the isolation or the purification of the intermediate compounds. Furthermore, despite the fact that each of the above steps may be carried out according to conventional methods, the use of air and/or moisture sensitive reagents, for instance thionyl chloride, may thus require the adoption of reaction conditions rather troublesome, at least when operating with large amounts of substrates and reactants, as per the industrial scale.

By that, it would be particularly advantageous to find out an alternative way to prepare Iopamidol, in high yields and with a high degree of purity, by means of a process comprising reacting any suitable intermediate precursor with an alternative reactant to compound (4).

In this respect, examples for the preparation of given aromatic carboxamido compounds by reacting sulfinyl derivatives with α-hydroxyacids are reported in the literature. See, for instance, *Bioorg. Med. Chem. Lett.* 2006; 16; 4784-4787; and *Bioorg. Med. Chem. Lett.* 2007; 17; 6261-6265, wherein an α-hydroxyacid moiety is reacted with aromatic not sterically hindered sulfinyl substrates. Likewise, the reaction of given α-hydroxyacids with suitable sulfinyl derivatives, therein referred to as N-sulfinylamine or even N-sulfinylaniline derivatives, is also reported in *Tetrahedron Lett.* 2000; 41; 6017-6020; and *Tetrahedron Lett.* 1986; 27; 1921-1924.

Interestingly, all of the N-sulfinylanilines reported in the aforementioned prior art documents and presently referred to as Ar—N=S=O compounds rely, essentially, on rather simple molecules deriving from:

aniline itself, wherein Ar corresponds to phenyl;

mono-substituted anilines, wherein Ar corresponds to p-chloro-$C_6H_4$—, p-methyl-$C_6H_4$—, p-nitro-$C_6H_4$—; or di-substituted anilines, wherein Ar represents 2-fluoro-4-methoxycarbonyl-$C_6H_3$— or 2,4-dichloro-$C_6H_3$.

To our knowledge, however, such a synthetic method has never been disclosed for the preparation of given carboxamides, in a single step, by starting from sterically hindered compounds, in particular from N-sulfinylanilines fully substituted, namely penta-substituted on the aromatic ring. To this extent, it is worth noting that within the process for the preparation of Iopamidol, the aromatic ring of the above sulfinyl derivatives of formula (2) is fully substituted in positions 3 and 5 by two carbonyl moieties (e.g. —COCl groups) and, remarkably, in positions 2, 4 and 6 by three iodine atoms, known to be particularly bulky substituents.

We have thus found that sterically hindered fully-substituted N-sulfinylanilines are able to react, in a single step and under mild operative conditions, with suitable α-hydroxyacids or a salt thereof, to give the desired carboxamido derivatives, according to an alternative synthetic pathway.

SUMMARY OF THE INVENTION

The present invention thus provides a very advantageous process for the preparation of Iopamidol, by starting from commercially available α-hydroxyacids or a salt thereof, avoiding by that the above drawbacks related to the synthesis of (4).

Hence, it is an object of the invention a process for the preparation of a compound of formula

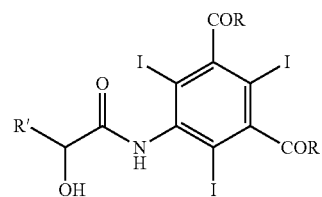

which process comprises reacting a compound of formula (II) with a α-hydroxyacid of formula (III), or a salt thereof, in the presence of a suitable base:

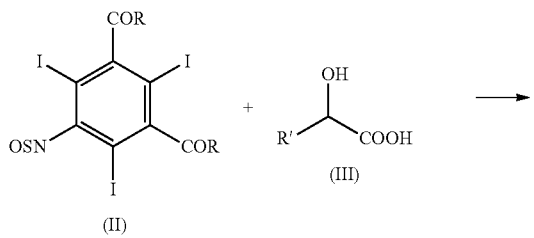

-continued

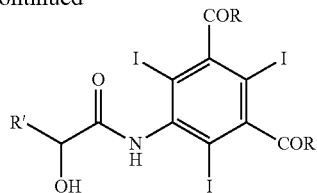

wherein:

R' is hydrogen or a straight or branched $C_1$-$C_6$ alkyl group optionally substituted by one or more protected hydroxy groups;

R is, the same in each occurrence, selected from the group consisting of alkoxy (—$OR_1$), amino (—$NH_2$ or —$NHR_1$) or a chlorine atom; and wherein $R_1$ is a straight or branched $C_1$-$C_6$ alkyl group optionally substituted by one or more protected hydroxy groups.

DETAILED DESCRIPTION OF THE INVENTION

According to a first embodiment, the present invention relies on a process for the preparation of a compound of formula (I), which process comprises reacting a compound of formula (II) with (2S)-2-hydroxy-propanoic acid, or a salt thereof, in the presence of a suitable base:

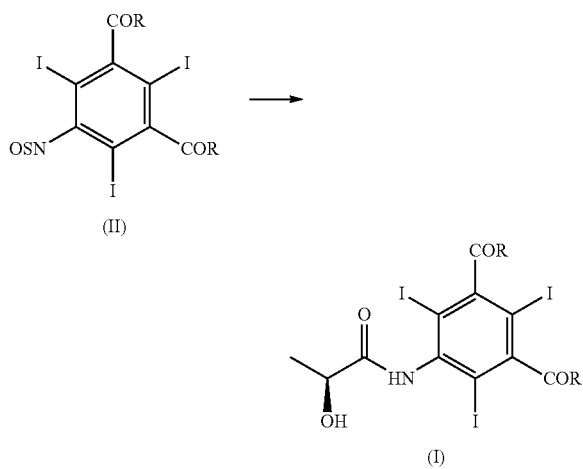

wherein:

R is, the same in each occurrence, selected from the group consisting of alkoxy —$OR_1$, amino —$NH_2$ or —$NHR_1$ or a chlorine atom; and wherein $R_1$ is a straight or branched $C_1$-$C_6$ alkyl group, optionally substituted by one or more protected hydroxy groups.

In addition, as detailed in the experimental section, the process of the invention enables the preparation of carboxamido derivatives with a conversion rate which is unexpectedly higher than that obtained with the corresponding non iodinated substrates.

The present invention thus relies on a new process for the synthesis of aromatic carboxamides and derivatives thereof by reacting tri-iodinated penta-substituted N-sulfinylanilines with a suitable α-hydroxyacid or a salt thereof.

The above process is particularly advantageous as it enables the preparation of the compounds of formula (I) in high yields and purity, without the need of reacting the corresponding anilino derivative with compound (4), the latter being prepared as formerly reported through a rather troublesome multistep process.

Importantly, as the compounds of formula (I) are optically active, the process of the invention takes in consideration their preparation by starting from the corresponding optically active α-hydroxyacid precursor, or a salt thereof, by fully retaining the optical configuration during the course of the reaction.

Clearly, the above process encompasses the preparation of the compounds of formula (I) according to any optical configuration at the asymmetric carbon atom (*) bearing the hydroxy group,

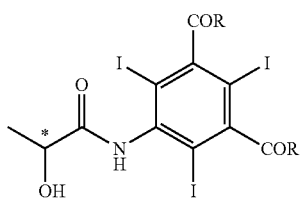

that is any (S) or (R) enantiomer or even any racemic (R,S) mixture thereof [each of which being also identified as (L), (D) or (L,D)] depending from the configuration of the lactic acid or salt being used.

According to the process of the invention, within the above compounds, R may represent an alkoxy group —$OR_1$ wherein $R_1$ is a straight or branched $C_1$-$C_6$ alkyl group, optionally substituted by one or more protected hydroxy groups. In addition, and unless otherwise provided, R may also represent an amino group —$NH_2$ or —$NHR_1$, wherein $R_1$ is as above reported, or a chlorine atom.

In the present description, unless stated otherwise, the term "straight or branched $C_1$-$C_6$ alkyl" means a linear or branched alkyl group with from 1 to 6 carbon atoms. Examples of them include, but are not limited to, methyl, ethyl, n-propyl, isopropyl, n-butyl, isobutyl, sec-butyl, tert-butyl, n-hexyl and the like.

By analogy, the term alkoxy —$OR_1$ relies on alkyl-oxy groups wherein alkyl is as formerly reported. Not limiting examples of straight or branched alkoxy groups include, e.g., methoxy, ethoxy, n-propoxy, isopropoxy, n-butoxy, isobutoxy, sec-butoxy, tert-butoxy, n-hexyloxy and the like.

With the term "protected hydroxy group" we refer, unless otherwise provided, to a hydroxy group suitably protected with a moiety selected among those widely known in the art, specifically intended to prevent the occurrence of any undesired reaction involving the free (e.g. unprotected) hydroxy group itself. Said selected protective group or moiety should not be of any obstacle during the overall process and, then, it should be easily removed to achieve the final product with the relevant hydroxy group (or groups) in an unprotected form. Not limiting examples of said protective groups are, among others, acyl groups including alkylcarbonyl, arylcarbonyl or arylalkycarbonyl groups wherein alkyl is as above defined. Preferably, the hydroxy protecting group is an alkylcarbonyl group such as acetyl (—$COCH_3$).

Moreover, under suitable circumstances, one single protective group may be efficiently employed for the protection of more than one hydroxy group, at the same time. Likewise, for instance in the case of vicinal diols, these latter may be suitably protected by the formation of intramolecular cyclic acetals or ketals, which may be easily cleaved as appropriate under known conditions.

For a general reference to protective groups in organic chemistry see, for instance, T. W. Green, Protective Groups in Organic Synthesis (Wiley, N.Y. 1981).

Accordingly, also in the case of carboxamides (I) and (II) wherein R is (—NHR$_1$) the said R$_1$ group may be optionally substituted by one or more, for instance one or two, protected hydroxy groups, as formerly reported.

Because all of the above, a few compounds are thus identified within formulae (I) and (II), for instance referable to isophthalic acid esters (e.g. when R═—OR$_1$) or even as isophthalic acid dichloride (e.g. when R═—Cl).

Likewise, in case R represents an amino group, isophthalic acid carboxamides (e.g. when R═—NH$_2$), for instance including N-alkylcarboxamides (e.g. when R═—NHR$_1$), are thus contemplated according to the process for the invention.

According to a preferred embodiment, the present invention refers to a process for the preparation of a compound of formula (I) by starting from a compound of formula (II), wherein R is a chlorine atom.

According to an additional preferred embodiment, the present invention refers to a process for the preparation of a compound of formula (I) by starting from a compound of formula (II), wherein R is —OR$_1$ and R$_1$ is as above defined. Even more preferably, R$_1$ is a straight or branched C$_1$-C$_4$ alkyl group, particularly methyl. According to a still additional preferred embodiment, the present invention refers to a process for the preparation of a compound of formula (I) by starting from a compound of formula (II), wherein R is —NH$_2$ or —NHR$_1$ and R$_1$ is as above defined.

More preferably, R$_1$ is a straight or branched C$_1$-C$_4$ alkyl group optionally substituted by one or more protected hydroxy groups.

Even more preferably, within this class, R$_1$ is a group —CH(CH$_2$OH)$_2$ wherein the hydroxy groups are suitably protected.

Compounds of formula (I) are useful contrast agents to be used in diagnostics, or precursors thereof, by suitably deprotecting any optional hydroxy group according to known methods.

Typically, for instance in the synthesis of Iopamidol, this latter may be obtained by deprotecting a corresponding compound of formula (I) wherein R is —NHR$_1$ and R$_1$ is —CH(CH$_2$OH)$_2$ wherein both hydroxy groups are protected, for instance as acetylated intermediates:

As formerly indicated, and according to an additional aspect of the invention, the present process is carried out by properly reacting the compound of formula (II) with (2S)-2-hydroxypropanoic acid, or a salt thereof.

Suitable examples of the above salts include alkali metals or alkaline-earth metals salts, preferably sodium, lithium or potassium salts.

Even more preferably, the process of the invention is carried out in the presence of the sodium salt, commercially available with a high degree of optical purity.

According to the stoichiometry of the reaction, the molar ratio between the sulfinyl substrate of formula (II) and the α-hydroxyacid or a salt thereof should be of at least 1 to 1.

Preferably, however, the reaction is carried out in the presence of an excess of the selected α-hydroxyacid or salt.

Both the aromatic substrate of formula (II) and the selected α-hydroxyacid or a salt thereof are reacted in the presence of a base such as, for instance, any suitable organic base.

Preferred examples of such a base are, e.g., imidazole, 1H-benzotriazole or 1,2,4-triazole, the latter being particularly preferred.

Typically, the molar amount of base over the starting material (II) will range from about 10% to about 150%, for instance of about 110%.

As regards the operative conditions, and unless otherwise provided, the instant process is carried out in the presence of a suitable solvent, preferably an aprotic solvent among those conventionally adopted in organic synthesis. We refer, for instance, to N,N-dimethylacetamide (DMAC), N,N-dimethylformamide (DMF), dimethylsulfoxide (DMSO), N-methyl-2-pyrrolidone (NMP), acetonitrile (CH$_3$CN), dichloromethane (DCM), and the like, as well as possible mixtures thereof. Preferably, the reaction is performed in the presence of DMAC or DMSO.

In line with the present process for the preparation of x-ray contrast agents or intermediates thereof, the reaction of compounds (II) to give the products (I) is carried out at a temperature ranging from about 0° C. to about 40° C., more preferably at room temperature, that is from about 20° C. to about 25° C.

The reaction time may vary from about 1 to about 10 hours, although the reaction is usually completed in about 4 hours.

According to an optional aspect of the invention, the process for the preparation of the compounds (I) may also be carried out in the presence of a proper catalyst that, whenever required, may be used to increase the rate of conversion of compound (II) to (I). Suitable examples of catalysts include phase transfer catalysts such as, for instance, ammonium quaternary salts whereas tetrabutyl ammonium bromide ([N(Bu)$_4$]$^+$Br$^-$) is preferred.

The starting materials of the present process are known in the art and may be prepared in accordance with conventional methods, for instance as reported in the following sections. Likewise, any additional reactant or solvent, also including the optional catalyst, are known and conventionally adopted in organic syntheses.

In a practical preferred experimental procedure, the process of the invention can be carried out as follows.

In a reactor equipped with a magnetic stirrer and a temperature probe, kept under an inert gas atmosphere, a proper amount of compound (II) is dissolved in an appropriate aprotic solvent system, at the selected temperature.

A suitable amount of base, optionally together with an appropriate catalyst, is added to the reaction mixture, and then stirred until a solution is obtained. A given amount of (L)-lactic acid or a salt thereof, is added to the mixture and the suspension thus obtained is stirred for a period of time, for instance for few hours, up to completion of the reaction.

Reaction progression may be monitored according to conventional methods (e.g. through HPLC techniques).

The expected compound of formula (I) is obtained in high yields and purity, and it may be collected and purified according to conventional means. Alternatively, it may be directly processed to the final compound intended for diagnostic application, as the case may be.

In this respect, it is worth noting that the compounds of formula (I) wherein R are chlorine atoms, as useful intermediates for the synthesis of contrast agents, in particular of Iopamidol, may be obtained according to the present process, either by starting from the corresponding compound of formula (II), as extensively detailed above, or, alternatively, by starting from its precursor 5-amino-2,4,6-triiodoisophthalic acid, without the need of any purification of the intermediate of formula (II) thus obtained.

Hence, it is a further object of the present invention a process for the preparation of 5-[(2S)-2-hydroxypropionylamino]-2,4,6-triiodoisophthalic acid dichloride, said process comprising:
(a) reacting 5-amino-2,4,6-triiodoisophthalic acid with a suitable chlorinating agent to obtain a crude comprising 5-sulfinylamino-2,4,6-triiodoisophthalic acid dichloride; and
(b) treating the crude of step (a) with (2S)-2-hydroxy-propanoic acid, or a salt thereof, in the presence of a suitable base, as per the Scheme below:

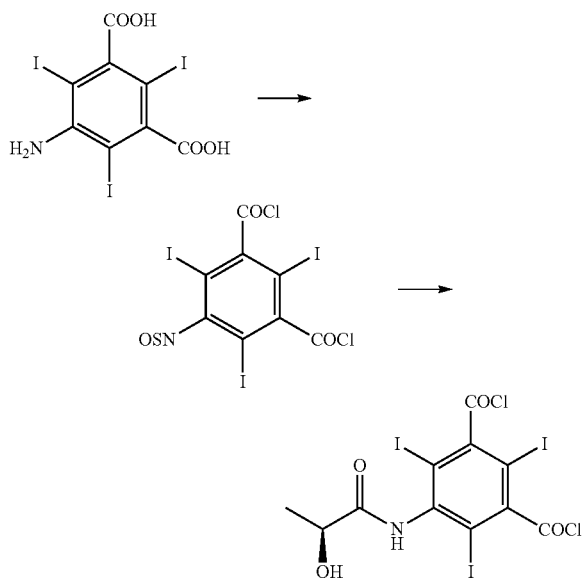

The above process is particularly advantageous as it enables to prepare the compound of formula (I) wherein R are chlorine atoms from the precursor 5-amino-2,4,6-triiodoisophthalic acid, a widely known intermediate for the synthesis of contrast agents.

The chlorinating agent provides for both conversions of the carboxy groups in the corresponding acyl chloride groups and, also, for the formation of the N-sulfinyl reactive group.

A variety of suitable chlorinating agents are known in the art and may be used in the present process. Particularly preferred, among them, is thionyl chloride; see, for a general reference, GB1.472.050; Pillai et al. *J. Org. Chem.* 1994; 59; 1344-50 and Harrie J. M. et al. *Org. Proc. Res. Dev.* 1999; 3; 38-43.

The operative conditions of step (a) are widely reported in the art and comprise, for example, the reaction of the starting material with thionyl chloride, optionally in the presence of a tertiary amine as disclosed for instance in *Bull. Korean Chem. Soc.* 1990; 11; 494-496. Similarly, Chidambaram et al. (Organic Process Research & Development 2002, 6, 632-636) disclose the synthesis of a 4-aminosulfinyl compound by reaction of ethyl 4-amino-3-fluorobenzoic acid ester with $SOCl_2$, whereas DE1085648B (Lentia GMBH) disclosed the preparation, as intermediate, of 3-sulfinylamino-2,4,6-triiodobenzoic acid chloride, by reacting the 3-amino-2,4,6-triiodobenzoic acid with thionyl chloride.

A variety of solvents may be used in step (a), and preferably, the reaction is performed in an aprotic solvent selected from those commonly known in organic synthesis such as, inter alia, dichloromethane (DCM), toluene and the like (see for a general reference WO 96/37459).

Alternatively, step (a) may be carried out in the presence of thionyl chloride acting both as a reactant and as a solvent medium. Clearly, at the end of the reaction, any excess of thionyl chloride needs to be suitably removed according to conventional means, for instance by vacuum distillation.

Subsequent step (b) will then be carried out as formerly reported in details.

The starting material of the present process is known, and can be easily prepared according to conventional methods, e.g. by hydrogenation or even by chemical reduction of commercially available 5-nitroisophthalic acid, followed by the iodination of the aromatic ring (see as a general reference, WO96/37458).

Even further, the present invention refers to a process which may be efficiently applied in the industrial preparation of contrast agents, in particular Iopamidol.

Such convenient process though may lead to the final product in a straightforward manner, by a lower overall number of steps, if compared to the synthetic way illustrated in Scheme I.

Therefore, it is an additional object of the present invention a process for the preparation of Iopamidol by reacting 5-[(2S)-2-hydroxypropionylamino]-2,4,6-triiodoisophthalic acid dichloride, this latter being obtained as previously disclosed, with 2-amino-1,3-propanediol, said reaction being carried out according to conventional methods; see, for a general reference among others, WO 96/037460, U.S. Pat. No. 5,362,905, WO 97/047590, WO 98/24757, WO 98/028259 and WO 99/058494. The process of the present invention is of general applicability and, hence, it may be well applied to a variety of aromatic substrates to be suitably reacted with selected α-hydroxyacids or salts thereof.

The process of the present invention thus enables to prepare Iopamidol, according to the operative conditions extensively reported.

As previously cited, we found that sterically hindered substrates upon reaction with a α-hydroxyacid moiety (e.g. lactic acid) or a salt thereof lead to the condensation products in an even higher yield if compared to the corresponding non iodinated and partially substituted aromatic starting material. As outlined in the Examples 1 and 2 of the following experimental section, the conversion yield of sulfinyl derivatives to the corresponding amido derivatives drops from 88.8%, when considering the tri-iodinated substrate as starting material, to 33.6% for the less hindered not iodinated substrate.

The following examples are herewith intended to better illustrate the process of the present invention, without posing any limitation to it.

EXPERIMENTAL PART

Reaction products, as per the following examples, were analyzed by HPLC techniques, as follows:

Column: FLUOPHASE PFP (perfluorophenyl) 100 Å 5 μm, 250×4.6 mm
Temperature: 40° C.
Mobile phase: A: water; B: acetonitrile/methanol 85:15 gradient elution
Detection (UV): 245 nm

Example 1

Preparation of Compound (I) from Compound (II), Wherein R=—OCH$_3$

In a 100 mL reactor, equipped with magnetic stirrer and temperature probe and kept under nitrogen, compound (II) (10.44 g; 0.0165 mol) was dissolved in DMAC (45 mL) at 20-25° C. After heating the solution to 40° C., 1,2,4-triazole (1.20 g; 0.0175 mol) was added and the mixture was stirred until a solution was obtained. (2S)-2-hydroxy-propionic acid sodium salt (Sodium (L)-lactate, 1.96 g; 0.0175 mol) was added to the solution and the obtained suspension was stirred at 40° C. for 5 h.

The reaction was monitored by HPLC. At the end of the reaction, HPLC analysis of the mixture showed that the amount of product (I) corresponded to 88.8% (% HPLC area).

Example 2 (Comparative)

Preparation of the Derivative Corresponding to the Non Iodinated Compound (I) Wherein R=—OCH$_3$ The process of Example 1 was repeated on the corresponding non iodinated substrate 5-(N-sulfinylamino)isophthalic acid dimethyl ester (II).

In a 100 mL reactor, equipped with magnetic stirrer and a temperature probe and kept under nitrogen, non iodinated compound (II) (4.08 g; 0.016 mol) was suspended in DMAC (90 mL) at 20-25° C. After heating the suspension to 40° C., 1,2,4-triazole (1.20 g; 0.0175 mol) and sodium (L)-lactate (1.96 g; 0.0175 mol) were added and the mixture was stirred at 40° C. for 3 h.

The reaction was monitored by HPLC. At the end of the reaction, HPLC analysis of the mixture showed that the non iodinated compound (I) accounted for a 33.6% (% HPLC area).

A comparison between Examples 1 and 2 clearly provides that the process of the invention allows to obtain, unexpectedly, the desired compounds of formula (I) with a degree of conversion remarkably higher than that obtained with corresponding less hindered substrates.

Example 3

Preparation of the Compounds of Formula (I) from Corresponding Derivatives of Formula (II) Wherein R=—OCH$_3$, —Cl or —NHCH(CH$_2$OCOCH$_3$)$_2$ A variety of compounds of formula (I) were obtained by following the experimental procedure as per Example 1, with the reaction conditions indicated in the following Table 1.

TABLE 1

| | Experimental data | | | |
|---|---|---|---|---|
| Compound (I) | Base: substrate (II) (molar ratio) | Solvent | Time/Temp | Yield |
| R = —OCH$_3$ | 1,2,4-Triazole (0.5:1) | DMAC | 10 hrs 40° C. | 66.1% |
| | 1,2,4-Triazole (1.1:1) | DMSO | 1 hrs 40° C. | 66.0% |
| | Imidazole (0.5:1) | DMAC | 10 hrs 40° C. | 71.0% |
| | Imidazole (1.1:1) | DMAC | 10 hrs 40° C. | 76.7% |
| | 1H-Benzotriazole (0.5:1) | DMAC | 10 hrs 40° C. | 76.2% |
| | 1H-Benzotriazole (1.1:1) | DMAC | 10 hrs 40° C. | 76.7% |
| R = —Cl | 1,2,4-Triazole$^{(*)}$ (1.3:1) | DMAC | 4 hrs 20-25° C. | 61.7% |
| | 1,2,4-Triazole$^{(*)}$ (1.3:1) | DMAC | 2 hrs 40° C. | 51.2% |
| | 1,2,4-Triazole (1.1:1) | DMAC | 4 hrs 40° C. | 44.2% |
| | 1H-Benzotriazole$^{(*)}$ (0.13:1) | DMAC | 6 hrs 20-25° C. | 43.5% |
| | 1,2,4-Triazole$^{(*)}$ (1.3:1) | DMAC | 4 hrs 0° C. | 42.0% |
| R = —NHCH(CH$_2$OCOCH$_3$)$_2$ | 1,2,4-Triazole (1.1:1) | DMSO | 5 hrs 40° C. | 34.4% |

$^{(*)}$[N(Bu)$_4$]Bromide was added together with the base, in a catalytic amount of 10% vs starting material.

The invention claimed is:

1. A process for the preparation of a compound of formula

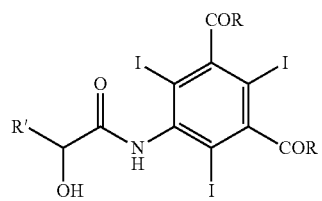

which process comprises reacting a compound of formula (II)

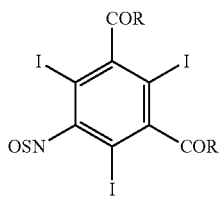

with a α-hydroxyacid of formula (III)

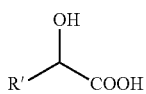

or a salt thereof, in the presence of a base,
wherein:
R' is hydrogen or a straight or branched $C_1$-$C_6$ alkyl group optionally substituted by one or more protected hydroxy groups;
R is, the same in each occurrence, selected from the group consisting of alkoxy (—$OR_1$), amino (—$NH_2$ or —$NHR_1$) and a chlorine atom;
$R_1$ is a straight or branched $C_1$-$C_6$ alkyl group optionally substituted by one or more protected hydroxy groups.

2. A process according to claim 1 for the preparation of a compound of formula I

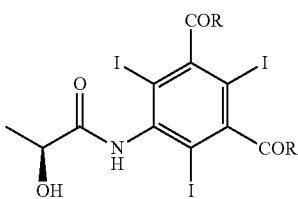

which process comprises reacting a compound of formula II with (2S)-2-hydroxy-propionic acid, or a salt thereof, in the presence of a suitable base, wherein R is, the same in each occurrence, selected from the group consisting of alkoxy (—$OR_1$), amino (—$NH_2$ or —$NHR_1$) and a chlorine atom; and $R_1$ is a straight or branched $C_1$-$C_6$ alkyl group optionally substituted by one or more protected hydroxy groups.

3. A process according to any one of claims 1-2 wherein R is a chlorine atom.

4. A process according to any one of claims 1 and 2 wherein R is —$OR_1$ and $R_1$ is a straight or branched $C_1$-$C_4$ alkyl group.

5. A process according to claim 4 wherein $R_1$ is methyl.

6. A process according to any one of claims 1-2 wherein R is —$NH_2$ or —$NHR_1$ and $R_1$ is a straight or branched $C_1$-$C_4$ alkyl group optionally substituted by one or more hydroxy protected groups.

7. A process according to claim 6 wherein $R_1$ is —CH($CH_2OCOCH_3$)$_2$.

8. A process according to claim 2 wherein the salt of the (2S)-2-hydroxy-propionic acid is selected from the group consisting of: lithium, sodium and potassium salt.

9. A process according to claim 8 wherein said (2S)-2-hydroxy-propanoic acid salt is a sodium salt.

10. A process according to any one of claims 1, 2 and 9 wherein the base is a heterocyclic base selected from imidazole, 1H-benzotriazole or 1,2,4-triazole.

11. A process according to claim 10 wherein the heterocyclic base is 1,2,4-triazole.

12. A process according to claim 1 carried out in the presence of a phase transfer catalyst.

13. A process according to claim 12 wherein the phase transfer catalyst is tetra butyl ammonium bromide.

14. A process according to claim 3 wherein compound II is obtained by reaction of 5-amino-2,4,6-triiodoisophthalic acid with a sulphur-containing chlorinating agent, and said compound II is immediately reacted with (2S)-2-hydroxy-propionic acid, or a salt thereof, to give 5-[(2S)-2-hydroxypropionylamino]-2,4,6-triiodoisophthalic acid dichloride of formula I.

15. A process for the preparation of Iopamidol comprising the process according to claim 14, and the subsequent reaction of the 5-[(2S)-2-hydroxypropionylamino]-2,4,6-triiodo-isophthalic acid dichloride thus formed, with 2-amino-1,3-propanediol.

* * * * *